US008637268B2

(12) United States Patent
Chen et al.

(10) Patent No.: US 8,637,268 B2
(45) Date of Patent: Jan. 28, 2014

(54) DETERMINATION OF VON WILLEBRAND FACTOR CLEAVAGE BY ADAMTS13

(75) Inventors: Junmei Chen, Seattle, WA (US); Dominic W. Chung, Bellevue, WA (US); Jose Aron Lopez, Seattle, WA (US)

(73) Assignee: Puget Sound Blood Center, Seattle, WA (US)

( * ) Notice: Subject to any disclaimer, the term of this patent is extended or adjusted under 35 U.S.C. 154(b) by 0 days.

(21) Appl. No.: 13/289,474

(22) Filed: Nov. 4, 2011

(65) Prior Publication Data

US 2012/0142036 A1 Jun. 7, 2012

Related U.S. Application Data (60) Provisional application No. 61/414,856, filed on Nov. 17, 2010.

(51) Int. Cl.
*C12Q 1/56* (2006.01)
(52) U.S. Cl.
USPC .......................................................... 435/13
(58) Field of Classification Search
USPC .......................................................... 435/13
See application file for complete search history.

(56) References Cited

U.S. PATENT DOCUMENTS

2005/0186646 A1* 8/2005 Cruz ............................ 435/7.92
2010/0136589 A1* 6/2010 Althaus et al. ................ 435/7.92
2010/0143957 A1* 6/2010 Varadi et al. .................... 435/18

OTHER PUBLICATIONS

Just S. Methodologies and Clinical Utility of ADAMTS13 Activity Testing. Seminars in Thrombosis and Hemostasis 36(1)82-90, Feb. 2010.*
Bowen J. An Influence of ABO Blood Group on the Rate of Proteolysis of von Willebrand Factor by ADAMTS13. J of Thrombosis and Haemostasis 1(1)33-40, Jan. 2003.*
Tripodi A. et al. Measurement of von Willebrand Factor Cleaving Protease ADAMTS13. J Thrombosis and Haemostasis 2(9)1601-9, Sep. 2004.*
Palla R. et al. Ristocetin Accelerates VWF Hydrolysis Rate and Ameliorates Collagen Binding Assay Sensitivity J Thrombosis and Haemostasis 3(Suppl 1)P0279, 2005.*
Kostousov V. et al. Novel Semiautomated 60 Minute Assay to Determine VWF Cleaving Activity of ADAMTS13 Thromosis Research 118:723-731, 2006.*
Veyradier A. et al. Assays of ADAMTS13 Activity Seminars in Hematology 41(1)41-47, Jan. 2004.*
Azuma, H. et al., "A Role for von Willebrand Factor Proline Residues 702-704 in Ristocetin-Mediated Binding to Platelet Glycoprotein Ib," Thrombosis and Haemostasis, 1993, pp. 192-196, 69, No. 2.
Berndt, M.C. et al., "Identification of Aspartic Acid 514 Through Glutamic Acid 542 as a Glycoprotein Ib-IX Complex Receptor Recognition Sequence in von Willebrand Factor. Mechanism of Modulation of von Willebrand Factor by Ristocetin and Botrocetin," Biochemistry, 1992, pp. 11144-11151, vol. 31, No. 45.
Chen, J. et al., "Interactions of Platelets with Subendothelium and Endothelium," Microcirculation, 2005, pp. 235-246, vol. 12, No. 3.
Dong, J-F. et al., "Ristocetin-Dependent, But Not Botrocetin-Dependent, Binding of von Willebrand Factor to the Platelet Glycoprotein Ib-IX-V Complex Correlates with Shear-Dependent Interactions," Blood, 2001, pp. 162-168, vol. 97, No. 1.
Girma, J.P. et al., "Ristocetin and Botrocetin Involve Two Distinct Domains of von Willebrand Factor for Binding to Platelet Membrane Glycoprotein Ib," Thrombosis and Haemostasis, 1990, pp. 326-332, vol. 64, No. 2.
Howard, M.A. et al., "Ristocetin —A New Tool in the Investigation of Platelet Aggregation," Thrombosis et Diathesis Haemorrhagica, 1971, pp. 362-369, vol. 26, No. 2.
Kang, M. et al., "Evidence from Limited Proteolysis of a Ristocetin-Induced Conformational Change in Human von Willebrand Factor That Promotes Its Binding to Platelet Glycoprotein Ib-IX-V," Blood Cells Molecules, and Diseases, 2008, pp. 433-443, vol. 40, No. 3.
Kao, K-J. et al., "Demonstration and Characterization of Specific Binding Sites for Factor VIII/von Willebrand Factor on Human Platelets," J. Clin. Invest., 1979, pp. 656-664, vol. 63, No. 4.
Sadler, J.E., "Redeeming Ristocetin," Blood, 2010, pp. 155-156, vol. 116, No. 2.
Veyradier, A. et al., "Risk of Myocardial Infarction in Carriers of Mutations in the Hemochromatosis-Associated Gene," Thromb Haemost, 2000, pp. 727-728, vol. 84, No. 4.

* cited by examiner

*Primary Examiner* — Ralph Gitomer
(74) *Attorney, Agent, or Firm* — Fenwick & West LLP (57) ABSTRACT Novel methods are described for measuring the rate of ADAMTS13-mediated cleavage of von Willebrand Factor (VWF) multimers. Through the use of the reagent, ristocetin, the method can advantageously be performed in the absence of an applied shear stress or added denaturing agent. Also described are methods for diagnosing ADAMTS13-associated disorders and methods for providing improved treatment of those disorders by evaluating the efficacy of the treatment using the methods as described.

24 Claims, 6 Drawing Sheets

DETERMINATION OF VON WILLEBRAND FACTOR CLEAVAGE BY ADAMTS13

CROSS REFERENCE TO RELATED APPLICATIONS

This application claims priority to U.S. provisional patent application No. 61/414,856, filed Nov. 17, 2010, the disclosure of which is hereby incorporated by reference in its entirety for all purposes.

STATEMENT OF GOVERNMENT SUPPORT

This invention was made with Government support of Grant No. RO1HL091153, awarded by the National Institutes of Health. The Government has certain rights in this invention.

FIELD

The present disclosure relates to the field of hematology. In particular, the present disclosure provides compositions and methods for analysis of ADAMTS13-mediated cleavage of von Willebrand Factor (VWF) and screening assays to identify agents that augment or inhibit the same. Also provided are diagnostic methods and kits for the diagnosis of ADAMTS13-associated disorders and methods for monitoring the treatment of ADAMTS13-associated disorders.

BACKGROUND

One important protein in primary hemostasis is von Willebrand Factor (VWF). Plasma von Willebrand Factor (VWF) is a multimeric protein that mediates adhesion of platelets to sites of vascular injury, and especially, the very large VWF multimers are hemostatically competent. The existence of plasma factors that control the size of VWF multimers has long been suspected. The von Willebrand Factor-cleaving protease ("VWFCP") is involved in the limitation of platelet thrombus growth by proteolytic cleavage of von Willebrand Factor multimers in humans (Furlan et al., Blood, 87:4223-4234 (1996)). Recently, the molecular structure of von Willebrand Factor-cleaving protease and the corresponding gene have been described (PCT App. Pub. No. WO 02/42441; Zheng et al., J Biol Chem, 276:41059-41063 (2001)) and have been identified as a new member of the ADAMTS family and designated ADAMTS13. VWFCP regulates VWF multimer size by proteolytic cleavage.

The large and ultra large VWF multimers play a central role in arterial thrombosis, whereby unusually large multimers of VWF have been seen in two similar forms of thrombotic microangiopathy—thrombotic thrombocytopenic purpura (TTP) and hemolytic-uremic syndrome (HUS)—both resulting in platelet aggregation leading to disseminated occlusions in the microcirculation. Patients with TTP have a deficiency of ADAMTS13, whereas patients with HUS show normal activity of the protease.

There are several types of TTP: an acute idiopathic or sporadic form, an intermittent form with an eventual relapse, and a chronic relapsing form. The rare hereditary form of TTP has been related to specific gene mutations in the ADAMTS13 locus. Acute idiopathic TTP or acquired TTP are usually more severe than chronic relapsing TTP, wherein these patients have acquired antibodies against ADAMTS13, which inhibit the von Willebrand Factor-cleaving protease (Furlan et al., Blood, 91:2839-2846 (1998); Furlan et al., N Engl J Med, 339:1578-1584 (1998)). TTP can be associated with autoimmune disorders, systemic infection, systemic malignancy, malignant hypertension, multiorgan failure, and congenital hemolytic anemia. TTP can initiate from events including: stem cell transplantation, pregnancy/postpartum, the administration of certain drugs, and bloody diarrhea. Intermittent relapsing TTP is also associated with the reappearance of ADAMTS13 inhibitor. For other forms of TTP, such as ticlopidine-associated TTP, it has also been observed that these patients have acquired antibodies against ADAMTS13 (Moake, N Eng J Med, 347:589-600 (2002)). However, some patients with acquired TTP having ultra large VWF multimers in plasma lack severely reduced levels of ADAMTS13.

Although TTP-like disorders have been associated with various medications, bone marrow transplantation, pregnancy, HIV infection, and autoimmune disease, most cases appear sporadically, without an obvious precipitating factor. This disease is seen most commonly in adults from 20 to 50 years old, with women affected slightly more often than men. In most TTP patients, the onset of the disease occurs in otherwise healthy individuals, and there is no history of a similar condition in other family members. However, in a smaller set of individuals, there is evidence suggesting that the condition can be inherited; and familial TTP has been reported in rare cases. In these cases, the disease begins early in life or sometime shortly after birth and is associated with multiple recurrences (i.e., a chronic relapsing course). The disease strikes about 4 out of every 100,000 people.

Current treatment consists of infusion of fresh frozen plasma with or without plasma exchange or plasmapheresis. In TTP, this treatment is repeated daily until blood tests show improvement. People who do not respond to this treatment, or who have frequent recurrences, can require removal of the spleen. Prior to the development of modern treatment protocols, fatality during an acute episode of TTP was greater than 90% (Rock et al., N Engl J Med, 325:393-397 (1991); George, Blood, 96:1223-1229 (2000)). Plasmapheresis has improved the outcome of this disease so that now 80 to 90% of patients recover completely; however, fatalities still occur. Although most incidents of the disease are acute, when relapses occur, the disease can become chronic.

Despite marked improvement in treatment outcome, the molecular pathogenesis of TTP is still unknown and the specific factor(s) responsible for the acute onset of this disease, or recovery following treatment, remains to be identified. Because the cause is unknown, there is no way to prevent the disease.

Existing diagnostic methods for ADAMTS13-related disorders such as TTP suffer from several limitations. For instance, most assays evaluate the activity of a subject's ADAMTS13 using substrates that are not endogenous to the subject. By failing to use the subject's own substrate, these methods fail to consider each of the relevant factors affecting the activity of ADAMTS13 for a particular subject. For instance, a subject's VWF can be resistance to cleavage by ADAMTS13, and this condition would go undetected by traditional diagnostic methods. Moreover, existing diagnostic methods generally require the application of shear stress or additional denaturing agents to induce ADAMTS13-mediated cleavage of VWF.

Therefore, a need exists in the art for improved ADAMTS13 activity assays, diagnostic methods for ADAMTS13-related disorders, and methods of evaluating the efficacy of treatment in individuals having ADAMTS13-related disorders. The present invention fulfills these needs.

SUMMARY

Platelet-bound VWF was recently demonstrated to be a better substrate for ADAMTS13, suggesting that exposure of the glycoprotein Ibα (GPIbα) binding site (A1 domain) also exposes the ADAMTS13-cleavage site (A2 domain). Because ristocetin induces von Willebrand factor (VWF) to bind GPIbα in stasis, we evaluated whether it could also enhance ADAMTS13 proteolysis of VWF. We used several VWF sources: plasma; purified plasma VWF; recombinant VWF fragments encompassing A1A2A3, A1A2, and two recombinant A2 domains, one containing a ristocetin-binding site (Asp1459-His1472) and the other lacking it. Ristocetin (1.0 mg/ml) accelerated ADAMTS13 cleavage of multimeric VWF and of each of the recombinant VWF fragments except for the A2 domain lacking the ristocetin binding site. We also examined the effect of ristocetin on the conformation of the A2 domain by assessing its effect on susceptibility of Met1606 at the ADAMTS13 cleavage site to oxidation by hypochlorous acid. Ristocetin markedly enhanced oxidation of Met1606, and of another A2 residue, Met1521. Together, these data indicate that exposure of the sites for GPIbα and ADAMTS13 are coupled, explaining why platelet-bound VWF is a better ADAMTS13 substrate and why enhanced proteolysis is often observed in type 2B von Willebrand disease.

Building upon the above described discoveries, the present disclosure addresses long felt needs in the art by providing novel methods for the analysis of ADAMTS13-mediated cleavage of VWF, methods for diagnosis of ADAMTS13-associated disorders, methods of evaluating the efficacy of treatment in subjects having ADAMTS13-associated disorders, and diagnostic kits for the diagnosis of ADAMTS13-associated disorders.

The present disclosure provides in a first aspect, methods for analyzing the von Willebrand Factor (VWF) cleaving activity of ADAMTS13 and variants thereof, comprising the steps of: providing multimeric VWF; contacting the multimeric VWF with ristocetin; contacting the multimeric VWF with ADAMTS13 or a variant thereof in the presence of ristocetin under conditions suitable for enzymatic cleavage of VWF; measuring a signal correlated with the rate of multimeric VWF cleavage by ADAMTS13; and determining the activity of the ADAMTS13 from the rate of multimeric VWF cleavage by ADAMTS13.

In an embodiment of this aspect, the method is performed in the absence of an applied shear stress.

In other embodiments of this aspect, the method is performed in the absence of an added denaturing agent.

In additional embodiments of this aspect, the method further comprises the step of providing a biological sample, wherein the biological sample comprises the multimeric VWF and the ADAMTS13.

In various embodiments of this aspect, the biological sample is a blood, serum, or plasma sample, to which ristocetin can be added.

In various embodiments of this aspect, the multimeric VWF and ADAMTS13 are not concentrated, purified, or isolated from the biological sample prior to measuring the signal correlated with the rate of multimeric VWF cleavage by ADAMTS13.

In other embodiments of this aspect, the multimeric VWF and ADAMTS13 are concentrated, purified, isolated, or a combination thereof from the biological sample prior to measuring the signal correlated with the rate of multimeric VWF cleavage by ADAMTS13.

In various embodiments of this aspect, the method further comprises the step of adding a test compound which modulates ADAMTS13-mediated cleavage of VWF, where the test compound can be one that inhibits cleavage of multimeric VWF. Alternatively, the test compound can augment cleavage of multimeric VWF. In an embodiment, the test compound is Factor VIII.

In a second aspect, the present disclosure provides methods for diagnosing an ADAMTS13-associated disorder in a subject, the method comprising the steps of: providing a first biological sample from the subject, wherein the sample comprises VWF and ADAMTS13; providing a second biological sample from a patient not having an ADAM-associated disorder, wherein the sample comprises VWF and ADAMTS13; contacting the first and second biological samples with ristocetin; measuring a first signal correlated with the rate of multimeric VWF cleavage by ADAMTS13 in the first biological sample; measuring a second signal correlated with the rate of multimeric VWF cleavage by ADAMTS13 in the second biological sample; determining the difference in the rate of multimeric VWF cleavage by ADAMTS13 in the first and second samples; and diagnosing the subject with the ADAMTS13-associated disorder when the difference in the rate of multimeric VWF cleavage by ADAMTS13 in the first and second samples is significant.

In an embodiment of this aspect, the method is performed in the absence of an applied shear stress.

In another embodiment of this aspect, the method is performed in the absence of an added denaturing agent.

In various embodiments of this aspect, the biological sample is a blood, plasma, or serum sample.

In an embodiment of this aspect, the multimeric VWF and ADAMTS13 are not concentrated, purified, or isolated from the first or second biological samples prior to measuring first and second signals.

In other embodiments of this aspect, the multimeric VWF and ADAMTS13 are concentrated, purified, isolated, or a combination thereof from the first or second biological samples prior to measuring the first and second signals.

In other embodiments of this aspect, the method further comprises the step of adding a test compound which modulates ADAMTS13 mediated cleavage of VWF. The test compound can be one that inhibits cleavage of multimeric VWF. Alternatively, the test compound can augment the cleavage of multimeric VWF. In some embodiments, the test compound is Factor VIII.

In some embodiments of this aspect, the difference is significant if the first and second rates of multimeric VWF cleavage by ADAMTS13 differ by more than 2%, 5%, or 10%.

In some embodiments of this aspect, the ADAMTS13-associated disorder is thrombotic thrombocytopenic purpura (TTP).

In other embodiments of this aspect, the ADAMTS13-associated disorder is characterized by resistance of VWF to cleavage by ADAMTS13.

In a further embodiment of this aspect, the resistance of VWF to cleavage by ADAMTS13 is caused by oxidation of an amino acid residue at the ADAMTS13 cleavage site on VWF, which can be Met-1606 or Met-1521.

Also provided are methods for monitoring treatment of a subject suffering from an ADAMTS13-associated disorder, the method comprising the steps of: administering a therapeutic agent to the subject; obtaining a biological sample from the subject, wherein the sample comprises VWF and ADAMTS13; contacting the biological sample with ristocetin; measuring a signal correlated with the rate of multimeric VWF cleavage by ADAMTS13; adjusting the therapeutic agent's dosage based on the determined rate of multimeric VWF cleavage; and administering the adjusted therapeutic agent dosage to the subject.

In various embodiments of this aspect, the therapeutic agent comprises ADAMTS13, Factor VIII, or a combination thereof.

In an embodiment of this aspect, the method is performed in the absence of an applied shear stress.

In another embodiment of this aspect, the method is performed in the absence of an added denaturing agent.

In various embodiments of this aspect, the biological sample is a blood, plasma, or serum sample.

In an embodiment of this aspect, the multimeric VWF and ADAMTS13 are not concentrated, purified, or isolated from the biological sample prior to measuring the signal.

In another embodiment of this aspect, the multimeric VWF and ADAMTS13 are concentrated, purified, or isolated from the biological sample prior to measuring the signal.

In a further embodiment of this aspect, the therapeutic agent's dosage is adjusted if the rate of multimeric VWF cleavage differs by more than 1%, 2%, or 5% from the rate occurring in a patient not having an ADAMTS13-associated disorder.

In some aspects of the present disclosure, diagnostic kits are provided for diagnosing an ADAMTS13-associated disorder, the kit comprising: ristocetin that is combinable with a biological sample, wherein the biological sample comprises VWF multimers and ADAMTS13; and an agent suitable for detecting VWF multimer cleavage products.

In an embodiment of this aspect, the kit further comprises a means of determining if the rate of VWF multimer cleavage by ADAMTS13 is abnormal.

In an embodiment of this aspect, the kit further comprises a second portion of ristocetin that is combinable with a second biological sample, wherein the second biological sample is a reference sample and comprises VWF multimers and ADAMTS13; and an agent suitable for detecting VWF multimer cleavage products in the second biological sample.

DETAILED DESCRIPTION

The present disclosure addresses long felt needs in the art by providing novel methods for the analysis of ADAMTS13-mediated cleavage of VWF, methods for diagnosis of ADAMTS13-associated disorders, methods of evaluating the efficacy of treatment in subjects having ADAMTS13-associated disorders, and diagnostic kits for the diagnosis of ADAMTS13-associated disorders.

The descriptions of various aspects of the invention are presented for purposes of illustration, and are not intended to be exhaustive or to limit the invention to the forms disclosed. Persons skilled in the relevant art can appreciate that many modifications and variations are possible in light of the aspect teachings.

It must be noted that, as used in the specification and the appended claims, the singular forms "a," "an" and "the" include plural referents unless the context clearly dictates otherwise. The definition of standard terminology can be found in reference works, including Sambrook et al., Molecular Cloning, A Laboratory Manual (1989) and Ausubel et al., Short Protocols in Molecular Biology (1999) 4th Ed., John Wiley & Sons, Inc. (as well as the complete version of Current Protocols in Molecular Biology). The practice of the present disclosure will employ, unless otherwise indicated, conventional methods of mass spectroscopy, protein chemistry, biochemistry, recombinant DNA techniques and pharmacology, all of which are within the skill of those in the art.

As used herein, the terms "subject" and "patient" are used interchangeably, and each encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The terms "subject" and "patient" do not denote a particular age or gender.

As used herein, the terms "treat" or "treatment" are used interchangeably and refer to either (i) a postponement of development of a disease and/or a reduction in the severity of such symptoms that will or are expected to develop or (ii) ameliorating existing symptoms, preventing additional symptoms, and ameliorating or preventing the underlying metabolic causes of symptoms. Treatment can be prophylactic (to prevent or delay the onset of the disease, or to prevent the manifestation of clinical or subclinical symptoms thereof) or therapeutic suppression or alleviation of symptoms after the manifestation of the disease.

As used herein, the term "therapeutic agent" and "test agent" are used interchangeably and refer to any agent that can be used to prevent, treat, or mitigate the effects of ADAMTS13-associated disorders or that modulates the ADAMTS13-mediated cleavage of VWF.

Von Willebrand Factor (VWF)

VWF is a plasma glycoprotein required for primary hemostasis. As an extracellular adapter molecule it mediates the adhesion of platelets to subendothelial collagen of a damaged blood vessel and platelet-platelet interactions in high shear-rate conditions. The concentration of mature VWF in plasma is approximately 10 µg/mL, and its half life is about 12 hours (Tomokiyo et al., Blood, 105:1078-1084 (2005); Nossent et al., J Thromb Haemost, 4:2556-2562 (2006)). VWF is synthesized in endothelial cells, where it is either secreted constitutively or stored in Weibel-Palade bodies for secretion upon stimulation, as well as in megakaryocytes, where it is stored in α-granules that later are partitioned into platelets (Ono et al., Blood, 107:528-534 (2006)). Subsequent to the synthesis of a precursor protein, VWF undergoes a number of intracellular processing steps. Building blocks of the VWF multimer are initially generated in a dimeric form by formation of a disulfide bond near the C-terminus By generation of disulfide bonds near the N-termini, the protein multimerizes to a gigantic protein with a molecular mass ranging over 3 orders of magnitude to more than 20,000 kDa (Sadler, Annu Rev Biochem, 67:395-424 (1998)). A single molecule can show the extraordinary length of several millimeters.

The pro-coagulant activity of VWF exhibits a non-linear function of size, since the larger the multimer, the more effective it is in promoting platelet adhesion exhibiting a critical effect on its function (Furlan, Ann Hematol, 72:341-348 (1996)). However, under shear stress conditions in the circulation the protein emerges more vulnerable to proteolytic digestion by ADAMTS13 (Lopez et al., Blood Coagul Fibrinolysis, 16 Suppl 1:S11-6 (2005)).

Regulation of VWF multimer composition in plasma is performed by two major cleaving events: first, ADAMTS13 proteolytically cleaves the A2 domain of each VWF monomer and second, thrombospondin-1 reduces the disulfide bonds interlinking VWF multimers (Tsai, Semin Thromb Hemost, 30:549-557 (2004)). In contrast to an irreversible fragmentation of VWF by ADAMTS13, the activity of thrombospondin-1 can regulate VWF size reversibly employing a reductase activity. Thrombospondin-1 is crucially involved in the predominant VWF cleavage by ADAMTS13 due to competition with ADAMTS13 for binding to the VWF A3 domain (Bonnefoy et al., Blood, 107:955-964 (2006)).

In the case of VWF deficiency, patients have a bleeding disorder called von Willebrand disease (VWD). Occurring in up to 1% of the general population, VWD is the most common hereditary bleeding disorder, of which several subtypes are recognized. Many cases remain undiagnosed because of the mild nature of bleeding in many patients and the fact that acute phase reactions can mask the diagnosis.

The term "VWF" or "recombinant VWF" or "rVWF" can be used interchangeably herein and refers to von Willebrand factor polypeptide.

The term "VWF cleavage fragment" or "VWF fragments" or "VWF cleavage products" are used interchangeably herein and refer to fragments of VWF which result from protease cleavage. In various aspects, the protease cleaving VWF is ADAMTS13. ADAMTS13, also called VWF-cleaving protease (VWFCP), is a zinc-containing metalloprotease enzyme that cleaves VWF. ADAMTS13 is secreted into blood and degrades large VWF multimers, decreasing their activity. ADAMTS13 contains of multiple structural and functional domains, and these domains can participate in the recognition and binding of ADAMTS13 to VWF.

The terms "VWF multimers," "multimers," or "multimer forms" are used interchangeably herein. The ultra large VWF (ULVWF) multimers are cleaved by ADAMTS13 as they are secreted from endothelial cells. Thus, the terms "ADAMTS13 and "VWFCP" are used interchangeably.

ADAMTS13

The terms "ADAMTS13," "recombinant ADAMTS13," and "rADAMTS13" can be used interchangeably and refer to a protein encoded by ADAMTS13, a gene responsible for familial TTP. Structural details and sequence information on ADAMTS13 can be found in Zheng et al. (Zheng et al., J Biol Chem, 276(44):41059-41063 (2001)), and said structure and sequence are hereby incorporated by reference. ADAMTS13 has been identified as a unique member of the metalloproteinase gene family, ADAM (a disintegrin and metalloproteinase). ADAMTS family members are distinguished from ADAMs by the presence of one or more thrombospondin 1-like (TSP1) domain(s) at the C-terminus and the absence of the EGF repeat, transmembrane domain and cytoplasmic tail typically observed in ADAM metalloproteinases. ADAMTS13 is known to possess VWF-cleaving protease activity.

The plasma ADAMTS13 in healthy individuals ranges from 0.5 mg to 1 mg per liter (Grunewald et al., Platelets, 13:451-458 (2002); Rock et al., Br J Haematol, 93:684-687 (1996)). ADAMTS13 consists of metalloprotease, disintegrin, first thrombospondin type 1 (TSP-1) repeat, Cys-rich and spacer domains (Moake et al., N Engl J Med, 307:1432-1435 (1982); Furlan et al., Baillieres Clin Haematol, 11:509-514 (1998)). The C-terminus of ADAMTS13 has additional TSP1 repeats and two CUB domains (Moake et al., N Engl J Med, 307:1432-1435 (1982); Furlan et al., Baillieres Clin Haematol, 11:509-514 (1998)). Previous studies have shown that the N-terminus of ADAMTS13 is necessary and sufficient for recognition and cleavage of denatured multimeric VWF (Fay et al., J Bioi Chem, 266:8957-8962 (1991); Horton et al., Gene, 77:61-68 (1989); Kaufman et al., Nucl Acids Res, 19:4485-4490 (1991)) or peptide substrate (GST-VWF73 or FRETS-VWF73) (Fay et al., J Bioi Chem, 266:8957-8962 (1991)). More recent studies have demonstrated that the spacer domain of ADAMTS13 binds the exosite (E-1660 APDLVLQR-1668) near the C-terminus of the VWF-A2 domain (Toso et al., J Biol Chem, 279: 21643-21650 (2004); Lankhof et al., Thromb Haemost, 81:976-983 (1999)). However, the role of the middle and distal C-terminal domains of ADAMTS13 in substrate recognition remains controversial.

ADAMTS13-Associated Disorders

The present disclosure relates to any disease or disorder associated with abnormal cleavage of VWF by ADAMTS13, which are well known to those of ordinary skill in the art. In particular, the term "ADAMTS13-associated disorder" refers to any disorder that is associated with the abnormal function of ADAMTS13-mediated cleavage of VWF, including without limitation defects arising from abnormal levels of ADAMTS13; abnormal activity of ADAMTS13; defects in the VWF substrate; or any other condition that affects the rate of ADAMTS13-mediated cleavage.

ADAMTS13 is the main physiological modulator of the size and adhesiveness of VWF in plasma. In patients with thrombotic thrombocytopenic purpura (TTP), a congenital or immune-mediated deficiency of ADAMTS13 reduces or abolishes the degradation of ultra large multimers of VWF (i.e., ULVWF) that cause the formation of intravascular platelet thrombi (thrombotic microangiopathy, TMA) (Moake, Clin Lab Sci, 11:362-364 (1998); Moake, N Engl J Med, 339:1629-1631(1998)), resulting in multiorgan failure very similar to that seen in severe sepsis (Gando et al., J Trauma, 47:719-723 (1999)). TTP can be associated with autoimmune disorders, systemic infection, systemic malignancy, malignant hypertension, multiorgan failure, and congenital hemolytic anemia. TTP can initiate from events including: stem cell transplantation, pregnancy/postpartum, drug association, and bloody diarrhea. Acquired TTP also occurs occasionally during pregnancy or in the postpartum period. Determination of ADAMTS13 activity in plasma and detection of auto-inhibitors is an evident diagnostic and therapeutic marker in TMA. In other thrombotic syndromes, for example, sepsis, associated disseminated intravascular coagulation, hemolytic uremic syndrome, venoocclusive disease after bone marrow transplantation and/or drug-induced thrombotic syndromes, an association with diminished ADAMTS13 activity is postulated (Mannucci et al., Blood, 98:2730-2735 (2001)).

More than 70 mutations in the ADAMTS13 gene have been reported in people with the familial form of TTP. Most of these mutations change single amino acids in the ADAMTS13 enzyme. Other mutations lead to the production of an abnormally small version of ADAMTS13 that cannot function properly. Mutations in the ADAMTS13 gene may severely reduce the activity of the ADAMTS13 enzyme. As a result, VWF is not processed normally in the bloodstream. If VWF is not processed normally by ADAMTS13, it promotes the formation of abnormal clots throughout the body by inducing platelets to stick together and adhere to the walls of blood vessels, even in the absence of injury. Additional factors such as pregnancy, diarrhea, surgery, and infection likely play a role in triggering abnormal clotting. Blood clots can block blood flow through small vessels, causing damage to the brain, kidneys, heart, and other organs. Abnormal clotting also causes other complications associated with TTP.

An altered ADAMTS13 activity is also postulated in connective tissue diseases like systemic lupus erythematosus or systemic sclerosis, pregnancy, bone marrow transplantation, acute and chronic inflammation, renal insufficiency and after treatment with vasoconstrictive peptide vasopressin or stabilized analogues.

In particular, the present disclosure relates to ADAMTS13-associated disorders, including but not limited to: thrombotic diseases, hemorrhagic diseases, inflammatory diseases especially systemic inflammatory diseases such as sepsis and/or infectious diseases caused by bacteria, viruses, parasites and/or fungi. Furthermore the present disclosure relates to any kind of disease or disorder associated with an altered VWF cleavage pattern, including but not limited to: burns, tissue damage caused by surgery or trauma, obstetric complications like HELLP syndrome, organ and/or bone marrow transplantation, thrombocytopenia-associated diseases such as autoimmune thrombocytoprenic purpura, chronic inflammatory disease like chronic bowel disease, scleroderma, systemic lupus erythematosis, rheumatoid arthritis, vasculitis or any kind of autoimmune disease. Furthermore metabolic diseases like diabetes mellitus, endocrine diseases, atherosclerosis and/or any kind of organ insufficiency due to microcirculatory failure.

Increased susceptibility to VWF proteolytic cleavage by ADAMTS13 appears to be responsible for the loss of large VWF multimers central to the pathophysiology of a different disease, type 2A von Willebrand disease (VWD) (Tsai et al., Blood, 89:1954-1962 (1997)). The same protease activity was subsequently shown to be deficient in the plasma of TTP patients (Tsai et al., N Engl J Med, 339:1585-1594 (1998); Furlan et al., N Engl J Med, 339:1578-1584 (1998)). It has been shown that most adults having TTP also have auto-antibodies circulating in the bloodstream (Tsai et al., N Engl J Med, 339:1585-1594 (1998); Furlan et al., N Engl J Med, 339:1578-1584 (1998)), as well as recent reports of antibodies against this protease which have been identified in a form of TTP associated with the antiplatelet drug ticlopidine (Tsai et al., Ann Intern Med, 132:794-799 (2000)). Despite the strong association of low VWF-cleaving protease activity with TTP, a direct causative link has not yet been established.

Assessment of the functional proteolytic activity of ADAMTS13 and the detection of ULVWF can be of major clinical relevance, since plasma exchange with enzyme-containing plasma preparations such as fresh frozen plasma (FFP), cryoprecipitate-poor plasma or the infusion of recombinant ADAMTS13 can restore the capacity to cleave ULVWF in the circulation.

Elevated plasma von Willebrand factor (VWF) and low ADAMTS13 activity have been reported in several inflammatory states, including sepsis and acute respiratory distress syndrome. One hallmark of inflammation is neutrophil activation and production of reactive oxygen species, including superoxide radical, hydrogen peroxide, and hypochlorous acid (HOC1). HOC1 is produced from hydrogen peroxide and chloride ions through the action of myeloperoxidase. HOC1 can oxidize methionine to methionine sulfoxide and tyrosine to chlorotyrosine. Notably, the ADAMTS13 cleavage site in VWF (i.e., the Tyr1605-Met1606 peptide bond) contains both oxidation-prone residues. Mass spectrometric analysis of ADAMTS13 substrates treated with HOC1 suggests that Met1606 is oxidized to the sulfoxide in a concentration-dependent manner, with complete oxidation at 75 M HOC1 (Chen et al., Blood, 115(3):706-712 (2010)). The oxidized substrates are cleaved much more slowly by ADAMTS13 than the nonoxidized substrates. Oxidation of the methionine at the ADAMTS13 cleavage site of VWF would be expected to produce a prothrombotic state, allowing the largest and most reactive multimers of VWF to persist in the circulation. It is of interest that another important regulator of thrombotic potential, thrombomodulin, can also be modified by methionine oxidation, abrogating its ability to act as a cofactor in the thrombin-catalyzed activation of protein C (Glaser et al., J Clin Invest, 90: 2565-2573 (1992)), which also gives rise to prothrombotic effects Inhibition of ADAMTS13-mediated cleavage of VWF multimers treated with HOC1 has been observed as well (Chen et al., Blood, 115(3):706-712 (2010)). Taken together, these findings suggest that reactive oxygen species released by activated neutrophils have a prothrombotic effect, mediated in part by inhibition of VWF cleavage by ADAMTS13.

Ristocetin

The term "ristocetin" as used herein means the glycopeptide antibiotic isolated from Nocardia lurida, which mimics the active constituent(s) of the exposed vessel wall and causes the binding of human VWF to human platelets and platelet agglutination. Included in this definition are those compounds that are functionally equivalent to ristocetin. Furthermore, the term comprises biochemically produced ristocetin or fragments thereof. Additionally, the term "functionally equivalent substances" comprises any substance that can replace ristocetin or fragments thereof as a non-physiological inducer of binding of VWF to GPIb (Furlan, Throat Haemost, 54:463-465 (1995)). In certain aspects of the present disclosure, it is contemplated that specific antibodies can be utilized in order to enhance the efficacy/potency of ristocetin, which in turn would allow the use of lower ristocetin concentrations (see e.g., Tornai, J Clin Invest, 91:273-282 (1993)).

Ristocetin is a peptide antibiotic from the soil bacterium Nocardia lurida. Ristocetin has been used for decades as a tool to diagnose deficiency or dysfunction of von Willebrand factor (VWF) in von Willebrand disease (Howard et al., Thromb Diath Haemorrh, 26(2):362-369 (1971); Kao et al., J Clin Invest, 63(4):656-664 (1979); Sadler, Blood, 116(2): 155-156 (2010)). Ristocetin can be used as a tool to assess the functional state of VWF because it induces the interaction of VWF with the platelet glycoprotein (GP) Ib-IX-V complex in the absence of shear stress or VWF immobilization, conditions normally required in vivo for their interaction (Chen et al., Microcirculation, 12(3):235-246 (2005)). Presumably, ristocetin facilitates the interaction by inducing an allosteric change in VWF that exposes the binding site for GPIbα (Dong et al., Blood, 97(1):162-168 (2001); Kang et al., Blood Cells Mol Dis, 40(3):433-443 (2008)). Ristocetin is one of two widely used modulators of the VWF-GPIbα interaction (the other being botrocetin). Ristocetin induces an interaction that most closely mimics shear-induced platelet adhesion and aggregation (Dong et al., Blood, 97(1):162-168 (2001); Veyradier et al., Thromb Haemost, 84(4):727-728 (2000)). Two binding sites for ristocetin have been identified within VWF flanking the platelet-binding A1 domain, Cys1237-Pro1251 and Glu1463-Asp1472 (Girma et al., Thromb Haemost, 64(2):326-332 (1990); Berndt et al., Biochemistry, 31(45): 11144-11151 (1992); Azuma et al., Thromb Haemost, 69(2): 192-196 (1993)). Both sites are proline-rich and brought into proximity by a disulfide bond between Cys1272 and Cys1458.

As demonstrated in the examples below, ristocetin has greater specificity than existing reagents for evaluating the activity of ADAMTS13 for cleaving multimeric VWF in vitro.

Increased Rate of ADAMTS13-Mediated Cleavage of VWF

Recently, Shim et al. (Shim et al., Blood, 111(2):651-657 (2008)) demonstrated that platelet-bound VWF was a better substrate for the plasma metalloprotease, ADAMTS13. Without being bound by any particular theory, it is theorized that the exposure of the GPIbα binding site on VWF could be coupled to exposure of the ADAMTS13 cleavage site. An additional factor may be the tensile force experienced by a given VWF strand with multiple bound platelets in a shear field which could be sufficient to stretch VWF and expose the ADAMTS13 cleavage site. For instance, force-induced exposure of this site has been demonstrated in several studies (Zhang et al., Science, 324(5932):1330-1334 (2009); Baldauf et al., J Thromb Haemost, 7(12):2096-2105 (2009); Wu et al., Blood, 115(2):370-378 (2010)).

Ristocetin induces von Willebrand factor (VWF) to bind platelet glycoprotein Ibα in stasis. As demonstrated in the examples below, the inventors have shown that ristocetin induces ADAMTS13 cleavage of purified VWF or VWF in plasma as efficiently as did 1.5 M urea and accelerated cleavage of A1A2A3 and isolated A2, but only when Asp1459-His1472 was present. Therefore, exposure of the sites for GPIbα and ADAMTS13 are coupled, explaining why platelet-bound VWF is a better ADAMTS13 substrate.

ADAMTS13 Activity Assays and Diagnosis of ADAMTS13-Associated Disorders

The present disclosure provides methods for analyzing ADAMTS13-mediated cleavage of VWF in vitro. The present disclosure also addresses a need in the art for improved methods for diagnosing ADAMTS13-associated disorders and for testing the effectiveness of new therapies in the treatment of ADAMTS13-associated disorders, including thrombotic thrombocytopenic purpura (TTP).

The present disclosure provides methods for analyzing the von Willebrand Factor (VWF) cleaving activity of ADAMTS13 and variants thereof, comprising the steps of: providing multimeric VWF; contacting the multimeric VWF with ristocetin; contacting the multimeric VWF with ADAMTS13 or a variant thereof in the presence of ristocetin under conditions suitable for enzymatic cleavage of VWF; measuring a signal correlated with the rate of multimeric VWF cleavage by ADAMTS13; and determining the activity of the ADAMTS13 from the rate of multimeric VWF cleavage by ADAMTS13.

In certain aspects, the method can be performed in the absence of an applied shear stress or added denaturing agent due to conformational change in VWF that is induced by ristocetin.

In various aspects, the sample that is measured can be blood, serum, or plasma. Unlike many existing methods, ristocetin can optionally be added directly to the biological sample without the need for further concentration, isolation, or purification of the plasma components of interest.

In certain aspects, a test agent can be added to the biological sample prior to analysis and the change in the rate of ADAMTS13-mediated cleavage of VWF can be assessed. The test agent can be any agent that would potentially modulate the rate of VWF cleavage by ADAMTS13, such as e.g., Factor VIII or an antibody to ADAMTS13.

Direct detection assays of proteolytic ADAMTS13 activity in biological samples are well known to those of ordinary skill in the art. The present disclosure provides improved methods for evaluating the ADAMTS13 activity for the diagnosis of ADAMTS13-associated disorders.

It is an object of the present disclosure to provide improved methods for the analysis ADAMTS13-mediated cleavage of von Willebrand Factor multimers (VWF). In various aspects, the present disclosure relates to diagnostic and therapeutic monitoring of several diseases in which reduced levels or activity of ADAMTS13 plays an etiologic and/or pathogenetic role. In these diseases (e.g., inflammatory, infectious and/or thrombotic diseases), variations of the concentration and/or activity and/or molecular state of VWF are essential for prognosis, diagnosis, therapy, and outcome. The methods of the present disclosure find use in coagulative diseases or altering physiological states especially characterized by decreased ADAMTS13 activity and/or pathologic platelet aggregation, as well as inflammatory diseases or altering physiological states such as systemic inflammatory response syndrome (SIRS) and/or sepsis and/or chronic inflammatory diseases.

According to the present disclosure, any suitable detection method can be used that is capable of evaluating variations in the rate of ADAMTS13-mediated cleavage of VWF. In certain aspects, the detection method can be vibrational spectroscopy, chemometrics (e.g., UV resonance, fluorescence, Raman spectroscopy or hierarchical cluster analysis for monitoring thrombotic and/or hemorrhagic diseases on the basis of different spectroscopic patterns). In certain aspects, the present disclosure includes the analysis of specific ADAMTS13 cleavage products. ADAMTS13-mediated cleavage can in some aspects be detected by SDS-PAGE and Western blot analysis using either a polyclonal anti-human VWF antibody or animal-derived monoclonal antibodies.

In certain aspects, the activity of the VWF-cleaving protease, ADAMTS13, can be measured by spectroscopic properties on the basis of a standard curve. In various aspects, the activity of ADAMTS13 can be evaluated in a subject's biological sample, e.g., by analyzing the spectroscopic pattern of the sample. Depending on the outcome of the analysis, the pathogenesis of several thrombotic diseases can be evaluated, for example by assessing the degradation status of VWF. The outcome of the analysis can also be used for disorder prognosis and can be associated with severity, therapeutic options and outcome of the disease. Several ADMTS13-associated disorders can be considered, for example, thrombotic diseases such as inflammatory, infectious and/or coagulatory diseases associated with altered VWF properties.

Additional assay methods include without limitation: collagen binding assays, ristocetin cofactor assays, electrophoretic analysis (e.g., multimer analysis) and immunological methods. Electrophoretic immunoassays, such as western blotting analysis, have largely been replaced by immunoradiometric assays (IRMA) and enzyme-linked immunosorbant assays (ELISA) (Laffan et al., Haemophilia, 10:199-217 (2004)). Several reports describe ADAMTS13 assays where the A2 domain of VWF is used as a substrate (Zhou et al., Thromb Haemost, 91:806-811 (2004); Kokame et al., Hemost Thromb Vasc Biol Blood, 103:607-612 (2004); Cruz et al., Thromb Haemost, 90:1204-1209 (2004)). Cleavage of the A2 domain can be monitored, for example, by an ELISA method.

In certain aspects, the present disclosure provides for methods of rapidly identifying subjects at risk of developing or persisting in a state comprising a deficiency and/or insufficient function of VWF cleaving substances like recombinant proteins with ADAMTS13-like proteolytic features; synthetic proteins with ADAMTS13-like proteolytic features; mutants, variants, fragments, and fusions of recombinant proteins with ADAMTS13-like proteolytic features; and mutants, variants, fragments, and fusions of synthetic proteins with ADAMTS13-like proteolytic features.

In another aspect, the present disclosure provides methods for diagnosing an ADAMTS13-associated disorder in a subject, the method comprising the steps of: providing a first biological sample from the subject, wherein the sample comprises VWF and ADAMTS13; providing a second biological sample from a patient not having an ADAM-associated disorder, wherein the sample comprises VWF and ADAMTS13; contacting the first and second biological samples with ristocetin; measuring a first signal correlated with the rate of multimeric VWF cleavage by ADAMTS13 in the first biological sample; measuring a second signal correlated with the rate of multimeric VWF cleavage by ADAMTS13 in the second biological sample; determining the difference in the rate of multimeric VWF cleavage by ADAMTS13 in the first and second samples; and diagnosing the subject with the ADAMTS13-associated disorder when the difference in the rate of multimeric VWF cleavage by ADAMTS13 in the first and second samples is significant.

In certain aspects, the difference in the rate of multimeric VWF cleavage by ADAMTS13 in the first and second samples is significant if it is greater than 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 100%. In certain aspects, the difference in rates of ADAMTS13-mediated cleavage is significant if the difference is greater than 2%. In further aspects, the difference in rates of ADAMTS13-mediated cleavage is significant if the difference is greater than 5%. In yet further aspects, the difference in rates of ADAMTS13-mediated cleavage is significant if the difference is greater than 10%.

In certain aspects, the present methods can be used to characterize the rate of ADAMTS13-mediated cleavage of VWF and to identify VWF substrates that are resistant to cleavage. The VWF substrate can be resistant to cleavage by ADAMTS13 for any reason such as genetic mutation or by the oxidation of the amino acid residues at the ADAMTS13 cleavage site (e.g., at the Tyr1605-Met1606 peptide bond of VWF). In particular, it is thought that the Met1606 residue of VWF can be oxidized by HOC1, thereby causing it to be resistant to cleavage by ADAMTS13.

In certain aspects, the method can be performed in the absence of an applied shear stress or added denaturing agent due to conformational change in VWF that is induced by ristocetin.

In various aspects, the sample that is measured can be blood, serum, or plasma. Unlike many existing methods, ristocetin can optionally be added directly to the biological sample without the need for further concentration, isolation, or purification of the plasma components of interest.

In certain aspects, a test agent can be added to the biological sample prior to analysis and the change in the rate of ADAMTS13-mediated cleavage of VWF can be assessed. The test agent can be any agent that would potentially modulate the activity of ADAMTS13, such as e.g., Factor VIII or an antibody to ADAMTS13. The effect of the test agent can have diagnostic significance.

In various aspects, the difference between the rate of VWF cleavage by ADAMTS13 in a subject and the rate in a normal individual is considered significant if the two rates differ by more than 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 100%. In certain aspects, the difference between the rate of VWF cleavage by ADAMTS13 in a subject and the rate in a normal individual is considered significant if the two rates differ by more than 1%. In further aspects, the difference is significant if it differs by more than 2%. In yet further aspects, the difference is significant if it differs by more than 5%.

In various aspects, the present disclosure relates to ADAMTS13-activity evaluation methods that can be used with a variety of biological samples including whole blood, serum, plasma, tissue and other body fluids of patients having or at risk of having ADAMTS13-associated disorders. In certain preferred aspects, the biological sample is plasma.

In certain aspects, ADAMTS13 activity is assessed in an unpurified biological sample. In further aspects, the components of the biological system are purified before the rate of ADAMTS13-mediated cleavage of VWF is assessed. Purification can include the use of cryoprecipitation, affinity chromatography, immuno-precipitation, or any other suitable purification method. Analyte purification can be performed, for example, to isolate target proteins from other plasma proteins such as albumin, immunoglobulin.

In certain aspects, the rate of ADAMTS13-mediated cleavage of VWF is assessed from recombinant cell culture samples. In certain aspects, standard biochemical techniques for protein isolation and purification can be used, including, but are not limited to, ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. In other aspects of the present disclosure, protein-refolding steps can be used as necessary to modify the conformation of the mature protein. In still other aspects of the present disclosure, high performance liquid chromatography (HPLC) can be employed for final purification steps.

In addition, ADAMTS13 or variants or other drugs based upon this protease can also be used in several different ways. ADAMTS13 or drugs developed from it can be used in normal individuals as a novel approach to effect anticoagulation (preventing abnormal blood clots). Since blood clots are the basis of many important human diseases including heart attack and stroke, ADAMTS13 is used itself or as a suitable platform for the development of new pharmaceuticals to treat these common human diseases, where the pharmaceuticals are anticoagulants. ADAMTS13 cleaves VWF in a specific conformation at the Tyr1605-Met1606 bond. It is believed that such "denaturation" is achieved in vivo by shear stress in the microvasculature. Using existing methods, this denatured conformation has been reproduced in vitro by slightly "denaturing" VWF in urea or guanidine and/or through the application of shear stress. Using the present methods, however, ristocetin is added to the biological sample and facilitates the binding between ADAMTS13 and VWF multimers by inducing conformational changes in VWF that expose the ADAMTS13 binding site.

The present disclosure provides a method for detecting and monitoring therapeutic effect for the treatment of ADAMTS13-associated disorders. In certain aspects, the present disclosure provides methods of drug monitoring for pharmaceutical compositions used for therapy of ADAMTS13-associated disorders such as thrombotic, hemorrhagic, inflammatory and/or infectious diseases which are characterized by abnormal levels of ADAMTS13 or aberrant ADAMTS13 activity. Significant changes in the rate of ADAMTS13-mediated cleavage of VWF as well as the functional and molecular properties of VWF after drug application indicate therapeutic efficacy of the active pharmaceutical ingredient.

Methods are provided for monitoring treatment of a subject suffering from an ADAMTS13-associated disorder, the method comprising the steps of: administering a therapeutic agent to the subject; obtaining a biological sample from the subject, wherein the sample comprises VWF and ADAMTS13; contacting the biological sample with ristocetin; measuring a signal correlated with the rate of multimeric VWF cleavage by ADAMTS13; adjusting the therapeutic agent's dosage based on the determined rate of multimeric VWF cleavage; and administering the adjusted therapeutic agent dosage to the subject.

In certain aspects, the method can be performed in the absence of an applied shear stress or added denaturing agent due to conformational changes in VWF that is induced by ristocetin.

In various aspects, the sample that is measured can be blood, serum, or plasma. Unlike many existing methods, ristocetin can optionally be added directly to the biological sample without the need for further concentration, isolation, or purification of the plasma components of interest.

In certain aspects, a therapeutic agent is administered to a subject. The therapeutic agent can be any agent that would potentially treat ADAMTS13-associated disorders, such as Factor VIII, ADAMTS13, or antibodies to ADAMTS13. In certain aspects, the therapeutic agent is Factor VIII, ADAMTS13, or a combination thereof.

Current treatment of diseases associated with a diminished rate of ADAMTS13-mediated cleavage of VWF consists of infusion of fresh frozen plasma with or without plasma exchange or plasmapheresis. In plasmapheresis, blood is withdrawn from the patient as for a blood donation. Then the plasma portion of the blood is removed by passing the blood through a cell separator. The cells are saved, reconstituted with a plasma substitute, and returned to the patient as a blood transfusion.

The identification of ADAMTS13 deficiency as the cause of TTP also has major implications for the treatment of this important human disease. The present disclosure provides methods of monitoring patients with TTP especially monitoring the administered therapeutically effective amount of a recombinant ADAMTS13 or genetic material comprising an ADAMTS13 gene or mutant or variant thereof.

Furthermore treatment can comprise administering a therapeutically effective amount of ADAMTS13 protease such that the symptoms of the disease are alleviated, wherein the ADAMTS13 protease is selected from the group consisting: recombinant ADAMTS13; synthetic ADAMTS13; mutants, variants, fragments, and fusions of recombinant ADAMTS13; and mutants, variants, fragments, and fusions of synthetic ADAMTS13.

The methods of the present disclosure find use in monitoring the treatment of diseases or altering physiological states characterized by decreased VWF-cleaving protease activity, resistance of VWF to cleavage, and/or pathologic platelet aggregation. The present disclosure provides methods for monitoring the increase in the rate of ADAMTS13-mediated cleavage of VWF and/or decreasing pathologic platelet aggregation by administering a therapeutic agent, for example, peptides or peptide fragments or variants of ADAMTS13. Alternatively, drugs which act to increase rate of ADAMTS13-mediated cleavage of VWF and/or decrease pathologic platelet aggregation are monitored through screening methods described above.

In certain aspects, the present disclosure provides a highly sensitive and specific method for screening individuals at risk of developing and/or presenting an ADAMTS13-associated disorder without any clinical symptoms.

In certain aspects, the present disclosure enables the evaluation of the molecular weight, function and structure of VWF as well as indirect detection of regulating agents in biological samples such as whole blood, serum, plasma, tissue and other body fluids for diagnostic and therapeutic strategies. Detection of spectra which are characteristic for high molecular and/or ultra large VWF is evident for a diminished proteolysis of VWF.

Sources of ADAMTS13 for use in the assays and methods of the present disclosure can be platelet rich plasma (PRP), platelet poor plasma (PPP), pooled normal plasma (PNP), isolated platelets, whole blood, tissue culture supernatant or purified ADAMTS13. The term "plasma" can include PRP, PPP and PNP.

As used herein, "normal platelets," "normal plasma," and "normal PRP," are derived from individuals who do not have either congenital TTP or acquired TTP. PNP is a mixture of plasma taken from multiple individuals who do not have TTP.

Measurements of ADAMTS13 activity are made in relation to "normal activity," that is, ADAMTS13 activity in normal platelets, normal plasma, normal platelet rich plasma (PRP), recombinant or purified ADAMTS13, and the like. Normal activity is considered the activity that would be exhibited by a subject not having an ADAMTS13-associated disorder. Thus, terms such as "reduced rate of ADAMTS13-mediated cleavage of VWF," "reduced ADAMTS13 activity," or "inhibited ADAMTS13 activity" refer to the rate of ADAMTS13-mediated cleavage of VWF and ADAMTS13 activity relative to the rate and activity measured in a normal sample, i.e., normal platelets, normal plasma, normal PRP, recombinant or purified ADAMTS13, and the like.

In various other aspects of the methods of the present disclosure, recombinant ADAMTS13 is administered to a subject. Recombinant human ADAMTS13 has been described (Plaimauer et al., Blood, 100:3626-3632 (2002)). In subjects with an inherited ADAMTS13 deficiency, normal human plasma is used as a source of ADAMTS13 and contains 1 U/mL of ADAMTS13. Purified plasma-derived or recombinant ADAMTS13 is currently available for use in animals at a dose range of 100-500 U/kg BW. The methods of the present disclosure contemplate the use of any of these sources administered at an appropriate dose of 1 U/mL or U/kg BW.

Kits

It is an object of the present disclosure to provide an assay kit for the detection of the rate of ADAMTS13-mediated cleavage of VWF. The kit can contain a subject's biological sample for assaying ADAMTS13 activity and a source of ristocetin. The kit can optionally include a reference sample with normal physiological ADAMTS13 activity and VWF cleavage activity. Furthermore the kit can optionally include reagents such as washing buffer, dilution buffer, and reagents for the concentration and/or isolation of VWF.

In some aspects, diagnostic kits are provided for diagnosing an ADAMTS13-associated disorder, the kit comprising: ristocetin that is combinable with a biological sample, wherein the biological sample comprises VWF multimers and ADAMTS13; and an agent suitable for detecting VWF multimer cleavage products. In further aspects, the kit further comprises a means of determining if the rate of VWF multimer cleavage by ADAMTS13 is abnormal. The rate of cleavage is be abnormal if it differs by more than 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 100% from that of an individual not having an ADAMTS13-associated disorder.

In further aspects, the diagnostic kit can further comprise a second portion of ristocetin that is combinable with a second biological sample, and an agent suitable for detecting VWF multimer cleavage products in the second biological sample, wherein the second biological sample is a reference sample and comprises VWF multimers and ADAMTS13.

EXAMPLARY ASPECTS

Below are examples of specific aspects for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

Example 1

Methods and Materials

Production of Recombinant ADAMTS13 and VWF Fragments

Recombinant ADAMTS13 (Ala75-Thr1427) and VWF fragments A1A2A3 (Asp1261-Ile1878), long A2 (Asp1459-Gly1674), and short A2 (Met1473-Gly1674) were expressed as fusion proteins with the pNBioSec vector (Mize et al., Protein Expr Purif, 57(2):280-289 (2008)) in HEK293 Tet-On cells as previously described (Chen et al., Blood, 115(3): 706-712 (2010)). In this expression system, recombinant proteins were secreted with dual tags: an N-terminal biotin-tag and a C-terminal protein C epitope tag. Serum-free-cell-culture medium containing the secreted recombinant proteins was concentrated 10-fold by centrifugation over an Ultra-10K filter and desalted over Sephadex G25.

ADAMTS13 Cleavage of Multimeric Von Willebrand Factor

Plasma VWF was purified from cryoprecipitate as described previously (Chen et al., Blood, 115(3):706-712 (2010)). Cleavage of recombinant VWF fragments by ADAMTS13 was carried out at 37° C. for 5 hours with or without modulators. The reactions were stopped by EDTA (final concentration 10 mM). Cleavage products were analyzed by electrophoresis in 4-15% gradient polyacrylamide gels (Bio-Rad Laboratories, Hercules, Calif.) after reduction. Cleavage products were transferred onto nitrocellulose membranes, blocked with 1% albumin in Tris-buffered saline with 0.05% Tween-20, probed with HRP-conjugated streptavidin (Thermal Scientific, Rockford, Ill.), and visualized with the Immobilon Western HRP substrate (Millipore).

Cleavage of purified VWF (2 µg/ml) by recombinant ADAMTS13 (0.4 µg/ml) was performed at 37° C. in the absence or presence of urea or ristocetin. The reactions were stopped at the indicated times with EDTA (final concentration 10 mM).

Cleavage of VWF by ADAMTS13 in citrated pooled normal plasma was examined by incubating 10-fold diluted plasma at 37° C. for various times. Monoclonal ADAMTS13 antibody or control antibody (final concentration: 20 µg/ml) was added to an aliquot of the diluted plasma. ADAMTS13 cleavage was stopped at indicated times with EDTA.

The VWF multimer pattern was evaluated by 1.5% agarose gel electrophoresis followed by Western blotting with a HRP-conjugated polyclonal VWF antibody (Dako, Inc., Carpinteria, Calif.) previously described (Chen et al., J Clin Invest, Submitted (2010)).

ADAMTS13 Cleavage of Von Willebrand Factor fragments

Cleavage of recombinant VWF fragments (1 µg/ml) by ADAMTS13 (0.15 µg/ml) was carried out at 37° C. for 5 hours in the presence of either 1.5 M urea, or 1.5 mg/ml ristocetin. The reactions were stopped by EDTA. Cleavage products were analyzed by electrophoresis in 4-15% gradient polyacrylamide gels after reduction. Cleavage products were transferred onto nitrocellulose membranes, blocked with 1% albumin in Tris-buffered saline with 0.05% Tween-20, probed with HRP-conjugated streptavidin, and visualized with the Immobilon Western HRP substrate.

Detection of Methionine Oxidation in VWF by Mass Spectrometry

Multimeric VWF was incubated with an HOCl-generating system containing 25 nM MPO plus $H_2O_2$ at various concentrations in PBS (pH 7.4) at 37° C. for 1 hr in the presence or absence of 1.0 mg/ml ristocetin. The oxidation reaction was stopped by the addition of excess free methionine. The oxidized protein was digested with trypsin and the peptides analyzed by nano liquid chromatography-electrospray ionization-tandem mass spectrometry (nanoLC-ESI-MS/MS).

Materials

The following materials were used in this study: ristocetin (American Biochemical and Pharmaceutical Ltd., Marlton, N.J.); hydrogen peroxide (VWR International, West Chester, Pa.); methionine (MP Biomedicals, Inc, Solon, Ohio); biotin, doxycycline, and vancomycin (Sigma-Aldrich, Inc, St. Louis, Mo.); sequencing-grade trypsin (Promega, Madison, Wis.); acetonitrile (J.T. Baker, Phillipsburg, N.J.); trifluoroacetic acid and formic acid (EMD, Merck KGaA, Darmstadt, Germany); rabbit anti-human VWF polyclonal antibody (Dako North America, Inc., Carpinteria, Calif.); monoclonal ADAMTS13 antibody (A10) and control antibody (Abcam, Cambridge, Mass.); myeloperoxidase (Athens Research Technologies, Athens, Ga.); FreeStyle 293 serum-free medium, puromycin (Invitrogen Corporation, Carlsbad, Calif.); HEK 293 Tet-On cells (Clontech, Mountain View, Calif.); and streptavidin-HRP (Thermal Scientific, Rockford, Ill.); Ultra-10K filter and Immobilon Western HRP substrate (Millipore, Billerica, Mass.); gradient polyacrylamide gels (Bio-Rad Laboratories, Hercules, Calif.); citrated pooled normal plasma (Precision BioLogic, Nova Scotia, Canada); Seakem gold agarose (Cambrex Bio Science Rockland Inc., ME); Sephadex G25 (GE Healthcare, Piscataway, N.J.); Finnigan LTQ linear ion trap mass spectrometer (Thermo Electron Corporation, San Jose, Calif.). Plasma VWF was purified from cryoprecipitate as described previously (Chen J. et al., Blood, 115(3):706-712 (2010)).

Example 2

Ristocetin Enhances ADAMTS13 Cleavage of VWF in the Absence of Shear Stress

It was evaluated whether ristocetin alone could enhance ADAMTS13 cleavage of VWF in the absence of shear force using both multimeric plasma VWF and recombinant monomeric VWF fragments. Four VWF sources were used for these experiments: plasma; purified, multimeric VWF from plasma; a recombinant fragment encompassing the three A domains (A1A2A3); and two recombinant A2 domains, one containing a previously identified ristocetin-binding site between D1459 and P1465, and the other lacking it.

Figure 1:
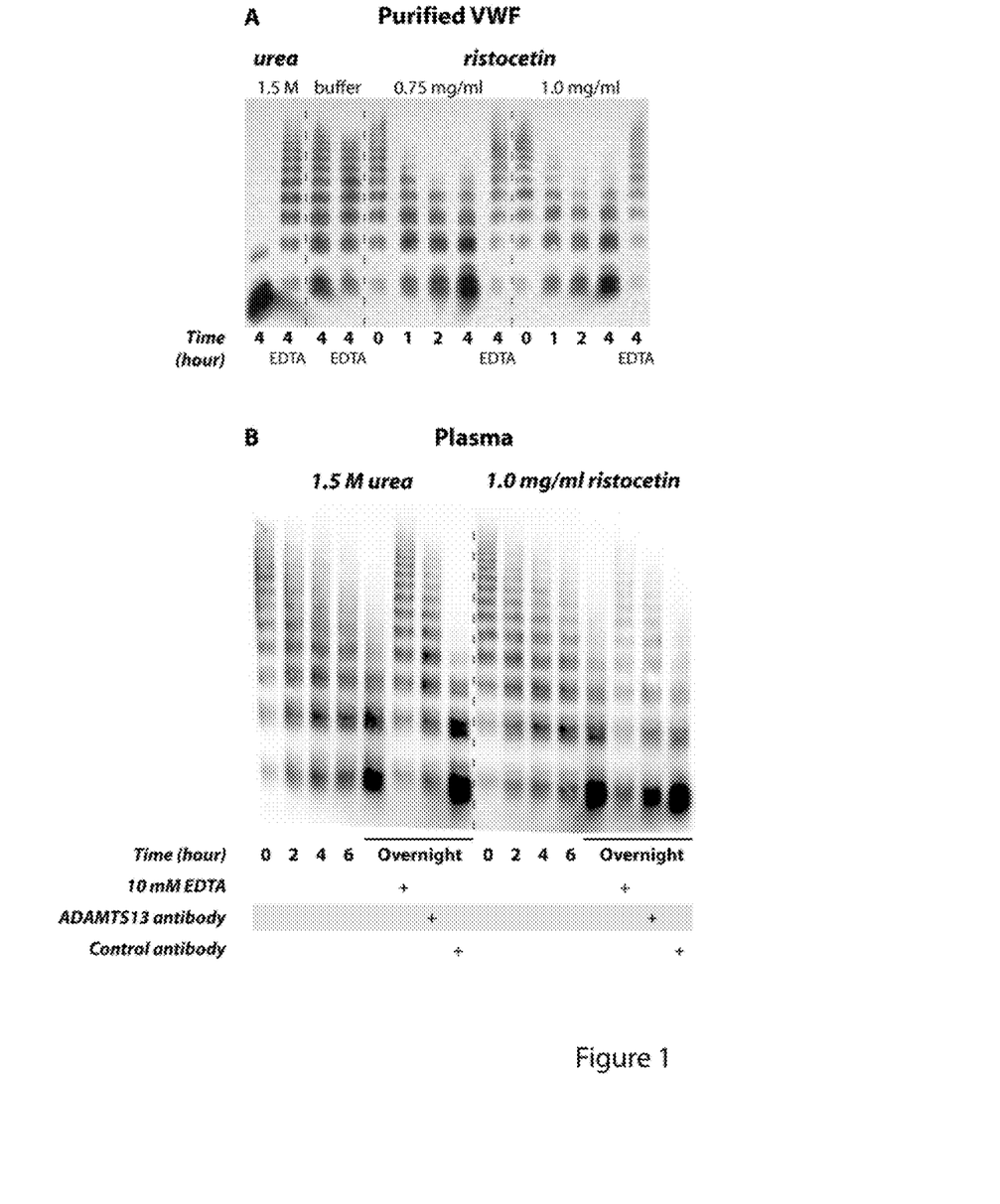
FIG. 1 shows that ristocetin enhances ADAMTS13 cleavage of multimeric VWF. A. Purified plasma VWF was incubated with recombinant ADAMTS13 at 37° C. in buffer only (10 mM HEPES and 6.5 mM $BaCl_2$, pH 7.4), urea, or ristocetin. For the samples labeled "EDTA", EDTA was added to the samples at time 0 and incubated at 37° C. for 4 hr. For the other samples, EDTA was added to stop ADAMTS13 cleavage at the indicated time. VWF multimer patterns were examined on a 1.5% agarose gel. B. Citrated pooled normal plasma was diluted 10-fold with buffer containing either urea or ristocetin, incubated at 37° C., and ADAMTS13 cleavage was stopped at indicated times with EDTA. VWF multimer patterns were examined on a 1.5% agarose gel.

Without being bound by any particular theory, it is theorized that VWF proteolysis is enhanced by platelet binding because bound platelets increase the tensile force applied to VWF strands in shear fields. Another is that exposure of the GPIbα and ADAMTS13 sites on VWF is allosterically coupled. Because ristocetin exposes the GPIbα-binding site, we evaluated its capacity to enhance ADAMTS13-mediated proteolysis of VWF under stasis (FIG. 1). At both 0.75 and 1.0 mg/ml, ristocetin accelerated the ability of recombinant ADAMTS13 to cleave purified multimeric plasma VWF (FIG. 1A). Similarly, ristocetin (1.0 mg/ml) added to diluted plasma enhanced the ability of endogenous ADAMTS13 to cleave VWF in a manner indistinguishable from the effect of 1.5 M urea (FIG. 1B), a denaturing agent used clinically to unfold VWF and potentiate its proteolysis (Furlan et al., Blood, 87(10):4223-4234 (1996)). Consistent with the responsible protease being ADAMTS13, proteolysis was inhibited by either a monoclonal antibody against ADAMTS13 or metal ion chelation with EDTA.

Example 3

Figure 2:
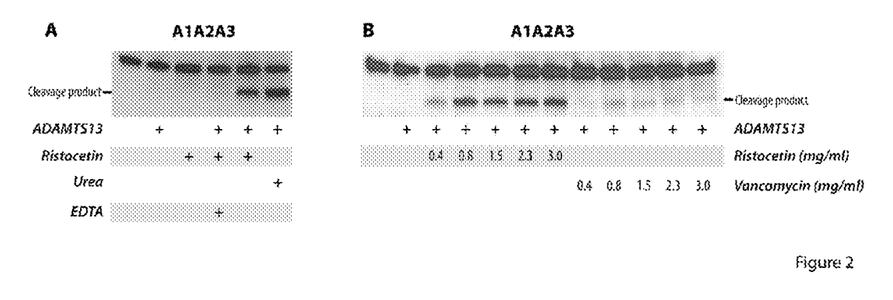
FIG. 2 shows that ristocetin, but not vancomycin, enhances ADAMTS13 cleavage of A1A2A3 in a concentration-dependent manner. A. A1A2A3 was incubated with ADAMTS13 in the presence of either urea, or ristocetin with or without EDTA at 37° C. for 5 hr. Cleavage products were detected by SDS-PAGE and western blotting. B. A1A2A3 was incubated with ADAMTS13 at 37° C. for 5 hr in the presence of increasing concentrations of ristocetin or vancomycin.

Ristocetin Enhances ADAMTS13 Cleavage of Recombinant VWF Fragments Containing the A2 Domain VWF is known to have only one cleavage site for ADAMTS13, the Tyr1605-Met1606 bond within the A2 domain. It was assessed whether ristocetin enhances cleavage of smaller recombinant fragments of VWF containing this site. Ristocetin induced ADAMTS13 to cleave a VWF fragment spanning the tandemly repeated A domains (A1A2A3), yielding a cleaved product of a size identical to that produced in the presence of urea (FIG. 2A). The minimum ristocetin concentration producing maximum proteolysis was approximately 0.8 mg/ml (FIG. 2B). The ristocetin effect was not mimicked by a related antibiotic, vancomycin.

Example 4

Figure 3:
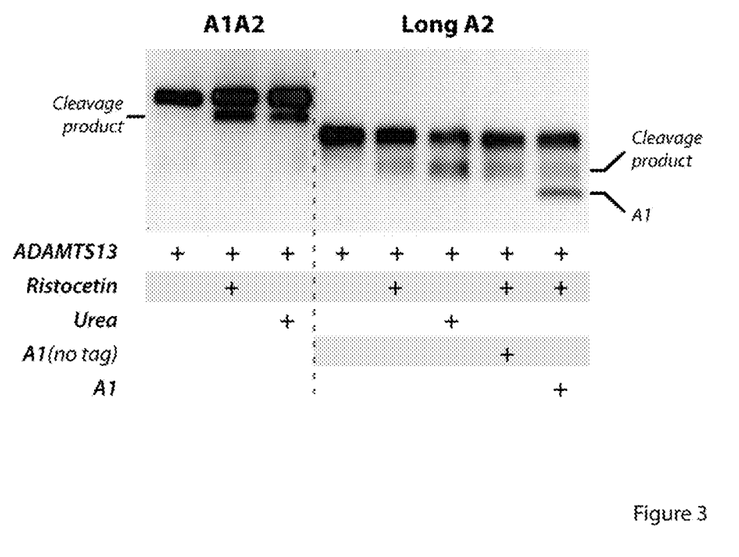
FIG. 3 shows the effect of the A1 domain on ADAMTS13 cleavage of A2 in the presence of ristocetin. Either A1A2 or long A2 was incubated with ADAMTS13 in the presence of either urea or ristocetin at 37° C. for 5 hr. On the right panel, isolated A1 with or without a biotin tag was added to aliquots of the reaction mixture. Cleavage products were detected by SDS-PAGE and western blotting.
Figure 4:
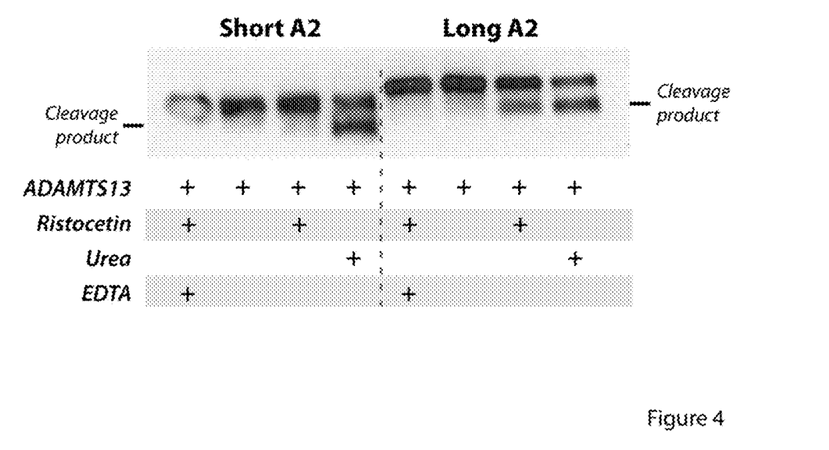
FIG. 4 shows that ristocetin requires the ristocetin-binding site within Asp1459-His1472 to induce ADAMTS13 cleavage in A2. The long and short A2 fragments were incubated with ADAMTS13 in the presence of either urea or ristocetin, with or without EDTA at 37° C. for 5 hr. Cleavage products were detected by SDS-PAGE and western blotting.

Minimum Sequence for Ristocetin to Expose the ADAMTS13-Cleavage Site in the A2 Domain Ristocetin is known to bind two sequences in VWF, Cys1237-Pro1251 at the N-terminus of the A1 domain and Glu1463-Asp1472, located between the A1 and A2 domains (Girma et al., Thromb Haemost 64(2):326-332 (1990); Berndt et al., Biochemistry 31(45):11144-11151 (1992); Azuma et al., Thromb Haemost 69(2):192-196 (1993)). We therefore sought to determine whether a known ristocetin-binding site was required for ristocetin to expose the ADAMTS13-cleavage site in the A2 domain. We compared ADAMTS13 cleavage of two recombinant proteins in the presence of ristocetin, an A1A2 fragment containing both ristocetin-binding sites and a long A2 fragment containing only the ristocetin-binding site located between the A1 and A2 domains. ADAMTS13 was able to cleave both fragments, indicating that the sequence Asp1459-His1472 was required for the ristocetin effect (FIG. 3). In support of this interpretation, ADAMTS13 was unable to cleave the A2 domain lacking the Asp1459-His1472 sequence (short A2) in the presence of ristocetin, but cleaved it normally in the presence of urea (FIG. 4).

Figure 5:
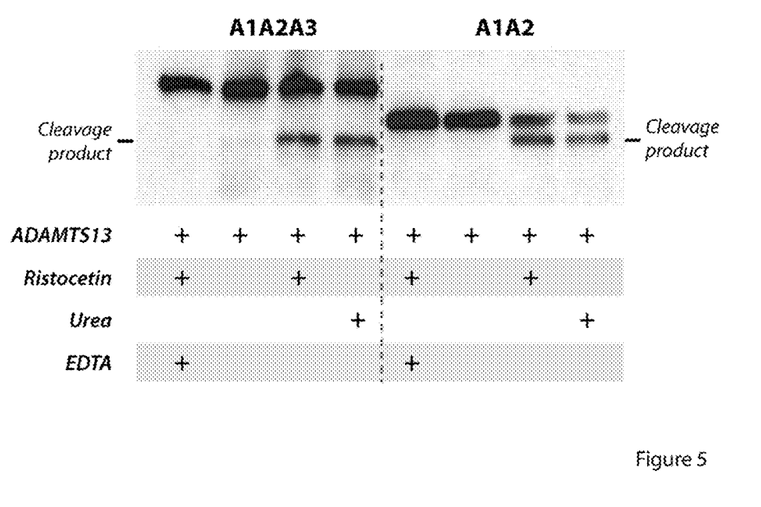
FIG. 5 shows the effect of the A3 domain on ADAMTS13 cleavage in A2 in the presence of ristocetin. A1A2A3 or A1A2 was incubated with ADAMTS13 in the presence of either urea or ristocetin with or without EDTA at 37° C. for 5 hr. Cleavage products were detected by SDS-PAGE and western blotting.

Ristocetin enhanced ADAMTS13 cleavage more efficiently in the A1A2 fragment than in the long A2 domain, but the A1 domain did not improve cleavage efficiency if it was not in the same polypeptide fragment as the A2 domain (FIG. 3). This phenomenon is unique to the A1 domain, because the presence or absence of the A3 domain had no significant effect on the ADAMTS13 cleavage of the A2 domain (FIG. 5).

Example 5

Figure 6:
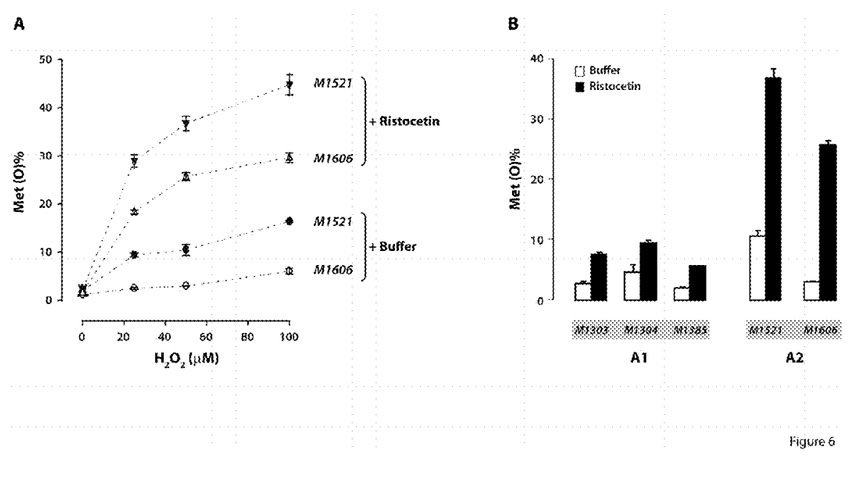
FIG. 6 shows that ristocetin enhances oxidation of Met1606 at the ADAMTS13 cleavage site. Multimeric VWF was incubated with an HOCl-generating system containing MPO and $H_2O_2$ in the presence of ristocetin or buffer. Methionine sulfoxide present in trytic peptides was analyzed by mass spectrometry. A. Percentage of methionine sulfoxide [Met(O)] at Met residues 1521 and 1606 in the A2 domain under various concentrations of $H_2O_2$ in the presence of 1.0 mg/ml ristocetin or buffer. B. Percentage of methionine sulfoxide [Met(O)] in the A1 and A2 domains in the presence of 25 nM MPO and 50 µM $H_2O_2$ with ristocetin or buffer.

Ristocetin Unfolds the A2 Domain and Enhances Oxidation of Met1606 at the ADAMTS13-Cleavage Site Met1606 at the ADAMTS13-cleavage site is buried within the A2 domain. Our data indicate that ristocetin can induce or expedite this unfolding, a process that may or may not be facilitated by ADAMTS13. We therefore also examined whether ristocetin could expose Met1606 in the absence of ADAMTS13, which we could evaluate by assessing the effect of ristocetin on hypochlorous acid-induced oxidation of Met1606. Multimeric VWF was incubated with an HOCl-generating system, MPO plus $H_2O_2$ of various concentrations, in the presence of ristocetin or buffer for 1 hr. The oxidized VWF was then digested with trypsin and methionine oxidation (methionine sulfoxide) in the A1 and A2 domains was examined by mass spectrometry as described previously. Two methionines buried in the A2 structure, Met1521 and Met1606, became more oxidized in the presence of ristocetin than in buffer (FIG. 6A), showing that ristocetin indeed changed the conformation of the A2 domain and exposed the two buried methionine residues to HOC1. Ristocetin also changed the conformation of the A1 domain, but the extent of oxidation was much less than in the A2 domain (FIG. 6B).

Ristocetin is known to induce GP Ibα-VWF dependent platelet aggregation by exposing the cryptic A1 domain in plasma VWF, faithfully mimicking the interaction induced by shear stress. Herein, we disclose that ristocetin also changes the conformation of the A2 domain, making the Tyr1605-Met1606 peptide bond available for ADAMTS13 cleavage or oxidation by HOC1. This effect required one of the ristocetin binding sites (Asp1459-His1472) located between the A1 and A2 domains, and was enhanced by the physically connected A1 domain.

These findings have several implications. First, they indicate that exposure of the sites in VWF for binding GPIbα and cleavage by ADAMTS13 within a single VWF subunit are coupled, explaining why elevated shear stress enhances both platelet binding and VWF proteolysis and partially explaining the finding of Shim et al. (Shim et al., Blood, 111(2):651-657 (2008)) that platelet-bound VWF is cleaved faster than unbound VWF. This effect undoubtedly also involves an increase in tensile stress on VWF, facilitating force-induced unfolding of A2, and exposure of the Tyr1605-Met1606 bond (Zhang et al., Science, 324(5932):1330-1334 (2009); Baldauf et al., J Thromb Haemost, 7(12):2096-2105 (2009); Wu et al., Blood, 115(2):370-378 (2010)). Simultaneous exposure of the GPIbα and ADAMTS13 sites is also consistent with the frequently observed increased VWF proteolysis associated with the gain-of-function phenotype of type 2B von Willebrand disease (Rayes et al., J Thromb Haemost, 5(2):321-328 (2007)). Second, the data also shed light on a potential mechanism of modulating exposure of the ADAMTS13 cleavage site. Previous studies have suggested that shear stress is the only means by which the ADAMTS13 cleavage site can be exposed in circulating VWF. A recent study estimated that 11 pN of force is needed to unfold a single A2 domain and that under a shear stress of 100 dyn/cm$^2$, a VWF multimer must contain at least 200 monomers to experience this amount of force in an A2 domain near the center of the polymer. A VWF polymer of this size has never been shown to exist in human blood. The effect of ristocetin found in our studies, requiring a short modulator sequence (Asp1459-His1472) but no applied force, indicates that exposure of the ADAMTS13 cleavage site may be modulated biochemically as well as mechanically, suggesting that both of these factors may be involved in VWF proteolysis in vivo. Finally, our findings also suggest that ristocetin might be a more specific reagent to evaluate the activity of ADAMTS13 for cleaving multimeric VWF in vitro.

It will be readily apparent to one of ordinary skill in the relevant arts that other suitable modifications and adaptations to the methods and applications described herein are suitable and can be made without departing from the scope of the invention or any aspect thereof. While the invention has been described in connection with certain aspects, it is not intended to limit the invention to the particular forms set forth, but on the contrary, it is intended to cover such alternatives, modifications and equivalents as can be included within the spirit and scope of the invention as defined by the following claims.

All references, issued patents, and patent applications cited within the body of the specification are hereby incorporated by reference in their entirety, for all purposes.

What is claimed is:

1. A method for analyzing the von Willebrand Factor (VWF) cleaving activity of ADAMTS13 and variants thereof, comprising the steps of:
   providing multimeric VWF, wherein the multimeric VWF is endogenous to a subject sample;
   contacting the multimeric VWF with ristocetin;
   contacting the multimeric VWF with ADAMTS13 or a variant thereof in the presence of ristocetin under conditions suitable for enzymatic cleavage of VWF;
   measuring directly the rate of multimeric VWF cleavage by ADAMTS13; and
   determining the activity of the ADAMTS13 from the rate of multimeric VWF cleavage by ADAMTS13.

2. The method of claim 1, wherein the method is performed in the absence of an applied shear stress.

3. The method of claim 1, wherein the method is performed in the absence of an added denaturing agent.

4. The method of claim 1, wherein the multimeric VWF is contained in a biological sample selected from the group consisting of a blood, serum, or plasma sample.

5. The method of claim 4, wherein the multimeric VWF and ADAMTS13 are not concentrated, purified, or isolated from the biological sample prior to measuring the signal correlated with the rate of multimeric VWF cleavage by ADAMTS13.

6. The method of claim 4, wherein the multimeric VWF and ADAMTS13 are concentrated, purified, isolated, or a combination thereof from the biological sample prior to measuring the signal correlated with the rate of multimeric VWF cleavage by ADAMTS13.

7. The method of claim 1, further comprising the step of adding a test compound which increases or decreases ADAMTS13-mediated cleavage of VWF.

8. A method of diagnosing an ADAMTS13-associated disorder in a subject, the method comprising the steps of:
   providing a first biological sample from the subject, wherein the sample comprises VWF and ADAMTS13;
   providing a second biological sample from a second subject not having an ADAM-associated disorder, wherein the sample comprises VWF and ADAMTS13;
   contacting the first and second biological samples with ristocetin;
   measuring directly a first rate of endogenous multimeric VWF cleavage by ADAMTS13 in the first biological sample;
   measuring directly a second rate of endogenous multimeric VWF cleavage by ADAMTS13 in the second biological sample;
   determining the difference in the rate of endogenous multimeric VWF cleavage by ADAMTS13 in the first and second samples; and
   diagnosing the subject with the ADAMTS13-associated disorder when the difference in the rates of endogenous multimeric VWF cleavage by ADAMTS13 in the first and second samples is significant.

9. The method of claim 8, wherein the method is performed in the absence of an applied shear stress.

10. The method of claim 8, wherein the method is performed in the absence of an added denaturing agent.

11. The method of claim 8, wherein the multimeric VWF is contained in a biological sample selected from the group consisting of a blood, plasma, or serum sample.

12. The method of claim 11, wherein the multimeric VWF and ADAMTS13 are not concentrated, purified, or isolated from the first or second biological samples prior to measuring first and second signals.

13. The method of claim 11, wherein the multimeric VWF and ADAMTS13 are concentrated, purified, isolated, or a combination thereof from the first or second biological samples prior to measuring the first and second signals.

14. The method of claim 8, wherein the difference is significant if the first and second rates of multimeric VWF cleavage by ADAMTS13 differ by more than 5% or more than 10%.

15. The method of claim 8, wherein the ADAMTS13-associated disorder is thrombotic thrombocytopenic purpura (TTP).

16. The method of claim 8, wherein the ADAMTS13-associated disorder is characterized by resistance of VWF to cleavage by ADAMTS13.

17. A method for monitoring treatment of a subject suffering from an ADAMTS13-associated disorder, the method comprising the steps of:
   administering a therapeutic agent to the subject;
   obtaining a biological sample from the subject, wherein the sample comprises VWF and ADAMTS13;
   contacting the biological sample with ristocetin;
   measuring directly the rate of endogenous multimeric VWF cleavage by ADAMTS13;
   adjusting the therapeutic agent's dosage based on the determined rate of endogenous multimeric VWF cleavage; and
   administering the adjusted therapeutic agent dosage to the subject.

18. The method of claim 17, wherein the therapeutic agent comprises plasma or plasma derivative.

19. The method of claim 17, wherein the method is performed in the absence of an applied shear stress.

20. The method of claim 17, wherein the method is performed in the absence of an added denaturing agent.

21. The method of claim 17, wherein the multimeric VWF is contained in a biological sample selected from the group consisting of a blood, plasma, or serum sample.

22. The method of claim 21, wherein the multimeric VWF and ADAMTS13 are not concentrated, purified, or isolated from the biological sample prior to measuring the signal.

23. The method of claim 21, wherein the multimeric VWF and ADAMTS13 are concentrated, purified, or isolated from the biological sample prior to measuring the signal.

24. The method of claim 17, wherein the therapeutic agent's dosage is adjusted if the rate of multimeric VWF cleavage differs by more than 5% or more than 10% from the rate occurring in a patient not having an ADAMTS13-associated disorder.

* * * * *

UNITED STATES PATENT AND TRADEMARK OFFICE
CERTIFICATE OF CORRECTION

PATENT NO. : 8,637,268 B2  Page 1 of 1
APPLICATION NO. : 13/289474
DATED : January 28, 2014
INVENTOR(S) : Junmei Chen, Dominic W. Chung and Jose Aron Lopez It is certified that error appears in the above-identified patent and that said Letters Patent is hereby corrected as shown below:

On the Title Page

Right Column, Item (56) line 2, after "Activity of ADAMTS13," delete "Thromosis," and insert -- Thrombosis --.

Signed and Sealed this
Twenty-first Day of October, 2014

Michelle K. Lee
*Deputy Director of the United States Patent and Trademark Office*